(12) United States Patent
Ball

(10) Patent No.: US 8,382,779 B2
(45) Date of Patent: Feb. 26, 2013

(54) VASCULAR CLAMPS FOR VASCULAR REPAIR

(75) Inventor: Geoffrey R. Ball, Axams (AT)

(73) Assignee: Vibrant Med-El Hearing Technology GmbH, Innsbruck (AT)

( * ) Notice: Subject to any disclaimer, the term of this patent is extended or adjusted under 35 U.S.C. 154(b) by 188 days.

(21) Appl. No.: 13/030,540

(22) Filed: Feb. 18, 2011

(65) Prior Publication Data

US 2011/0208218 A1 Aug. 25, 2011

Related U.S. Application Data

(60) Provisional application No. 61/306,689, filed on Feb. 22, 2010.

(51) Int. Cl.
*A61B 17/08* (2006.01)

(52) U.S. Cl. ........................................ 606/153

(58) Field of Classification Search .......... 606/153, 606/157, 158, 215–217, 201; 600/9, 12; 285/9.1, 205
See application file for complete search history.

(56) References Cited

U.S. PATENT DOCUMENTS

| | | | |
|---|---|---|---|
| 2,453,056 A * | 11/1948 | Zack | 606/153 |
| 3,254,650 A * | 6/1966 | Collito | 606/153 |
| 5,741,274 A | 4/1998 | Lenker et al. | 606/142 |
| 6,364,901 B1 | 4/2002 | Inoue | 623/1.13 |
| 2009/0149876 A1 | 6/2009 | Patel et al. | 606/151 |
| 2009/0163937 A1 | 6/2009 | Kassab et al. | 606/151 |

FOREIGN PATENT DOCUMENTS

WO  WO 2008/061024 A2  5/2008

OTHER PUBLICATIONS

European Patent Office, International Search Report and Written Opinion, PCT/US2011/025401, mailed Jun. 24, 2011.

* cited by examiner

*Primary Examiner* — Julian Woo
(74) *Attorney, Agent, or Firm* — Sunstein Kann Murphy & Timbers LLP

(57) ABSTRACT

A magnetic vascular clamp for vascular repair is described. There are two clamp pieces, where each clamp piece forms a partial cylindrical section of an annular cylinder. Each clamp piece has an outer surface and an inner surface, structural ribs arranged across the inner surface from one sectional end to the other, and a pair of magnetic sectional end surfaces connecting the outer surface and the inner surface and having a characteristic magnetic field arrangement. The sectional end surfaces and magnetic field arrangements of each clamp piece cooperate with the sectional end surfaces and magnetic field arrangements of the other clamp piece to form a complete annular cylinder held together by the magnetic field arrangements and enclosing an inner cylinder so as to structurally support damaged vascular tissue therein with minimal fluid leakage.

8 Claims, 6 Drawing Sheets

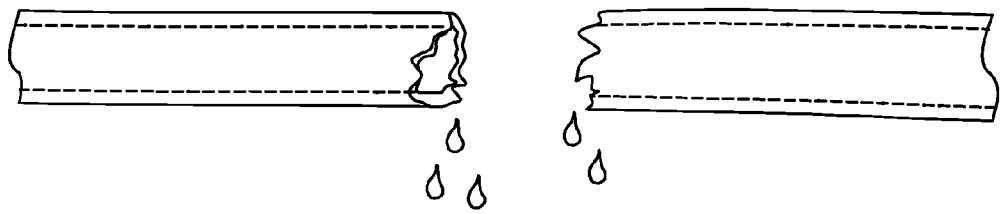
FIG. 1A
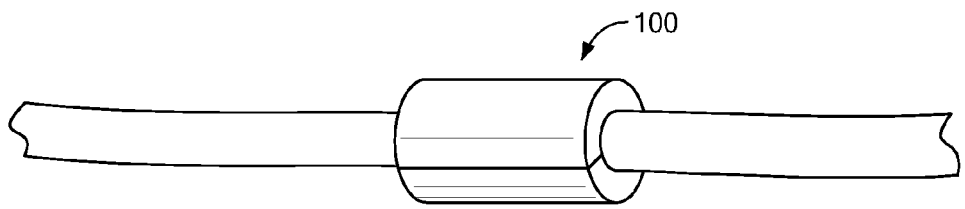
FIG. 1B
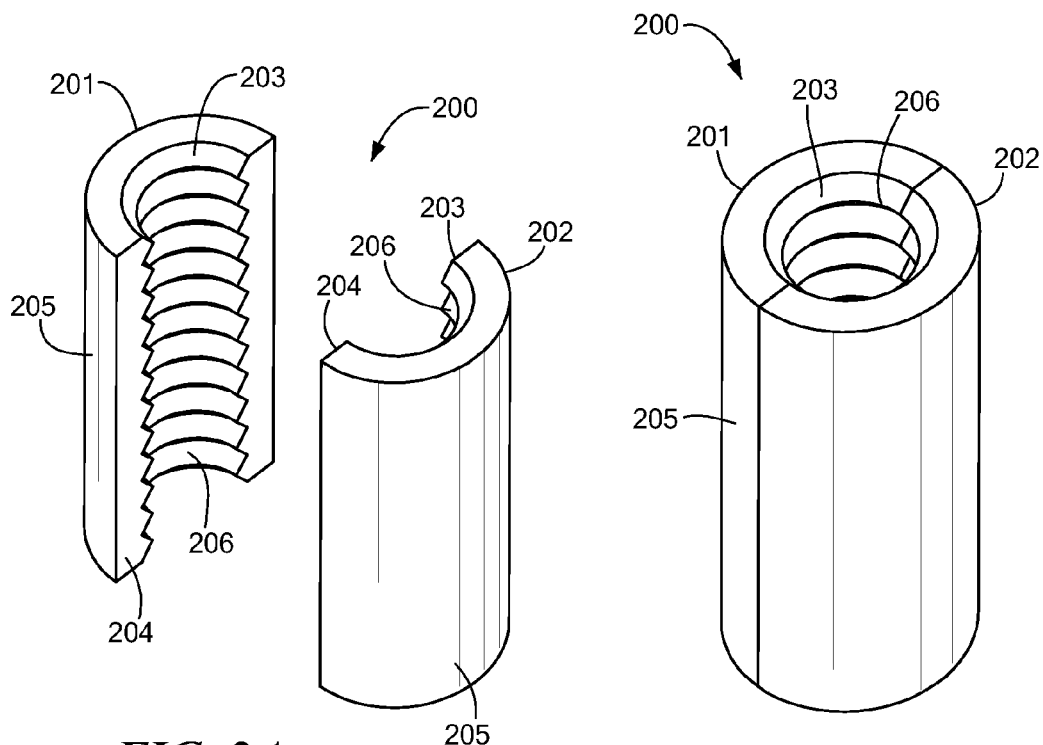
FIG. 2A
FIG. 2B

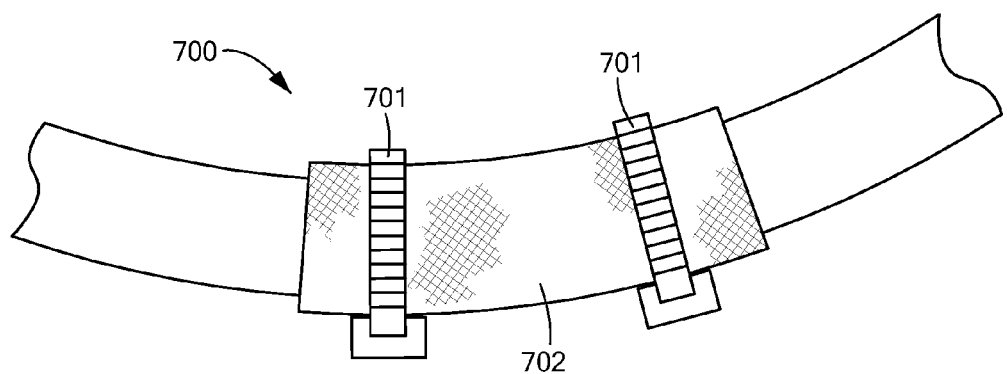
FIG. 7A
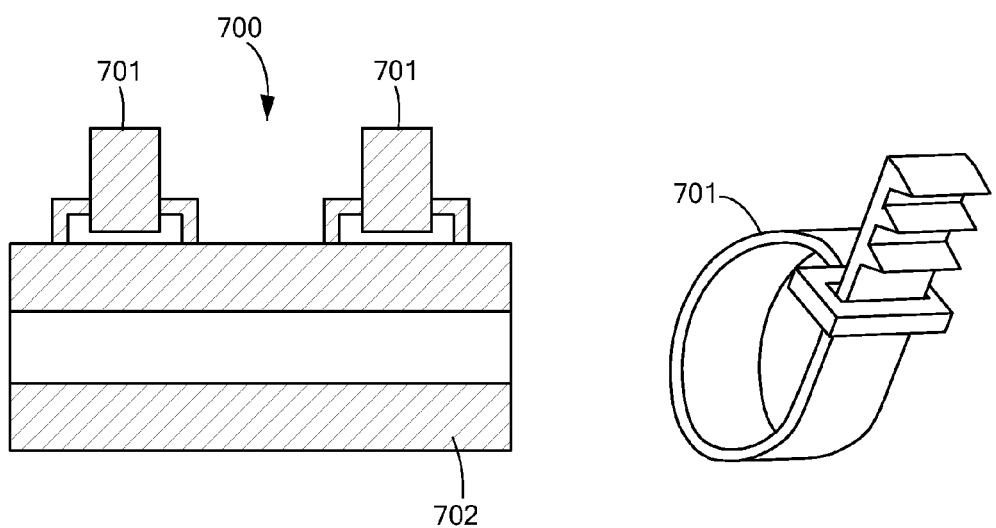
FIG. 7B          FIG. 7C

VASCULAR CLAMPS FOR VASCULAR REPAIR

This application claims priority from U.S. Provisional Application 61/306,689, filed Feb. 22, 2010; incorporated herein by reference.

FIELD OF THE INVENTION

The present invention relates to surgical devices, and more specifically to devices for use in repairing vascular structures in a patient.

BACKGROUND ART

Blood vessels are the body's equivalents of pipes for circulating blood to where it is needed. These vessels can become damaged or compromised, for example, due to injury-related trauma or during surgical procedures. Vascular clamps are devices that surround damaged vascular tissue to provide structural support while minimizing blood loss while repair surgery is performed.

SUMMARY OF THE INVENTION

Embodiments of the present invention are directed to a magnetic vascular clamp for vascular repair. There are two clamp pieces, where each clamp piece forms a partial cylindrical section of an annular cylinder. Each clamp piece has an outer surface and an inner surface, structural ribs arranged across the inner surface from one sectional end to the other, and a pair of magnetic sectional end surfaces connecting the outer surface and the inner surface and having a characteristic magnetic field arrangement. The sectional end surfaces and magnetic field arrangements of each clamp piece cooperate with the sectional end surfaces and magnetic field arrangements of the other clamp piece to form a complete annular cylinder held together by the magnetic field arrangements and enclosing an inner cylinder so as to structurally support damaged vascular tissue therein with minimal fluid leakage.

In specific embodiments, each magnetic field arrangement may include multiple magnetic field directions. Each clamp piece may include a magnetic rare earth magnet material such as samarium cobalt or neodymium for developing the magnetic field arrangements.

Some embodiments may further have an outer encapsulation layer (e.g., gold or titanium) covering some or all of each clamp piece. There also may be a therapeutic coating on the inner surface of each clamp piece to promote healing of the enclosed vascular tissue.

Embodiments of the present invention also include a vascular clamp for vascular repair having a flexible planar clamp surface that cylindrically encloses a section of vascular tissue with minimal fluid leakage, and at least one ratchet clamp having an end pawl and a plurality of ratchet teeth that cooperate in locking engagement to maintain the clamp surface around the enclosed vascular tissue.

In further such embodiments, there also may be a locking bar slidably engageable over the end pawl to lock the end pawl into the locking engagement with the ratchet teeth. In specific embodiments, the ratchet teeth may face radially inward towards the enclosed vascular tissue, while in other specific embodiments, the ratchet teeth may face radially outward away from the enclosed vascular tissue. In some embodiments, the ratchet clamp and the clamp surface may be integrated together into a single common structure. Or there may be a plurality of individual ratchet clamps that fit over the clamp surface.

Embodiments of the present invention also include a vascular clamp for vascular repair which has a vascular sleeve which forms a flexible cylindrical bellows that cylindrically encloses a section of vascular tissue to allow freely movement of the enclosed vascular tissue within the vascular sleeve. At each cylindrical end of the vascular sleeve there is a sleeve anchor ring that forms a fixed seal with underlying vascular tissue to minimize fluid leakage from within the vascular clamp.

In further such embodiments, each sleeve anchor ring may include a plurality of sealing ribs for sealing with the underlying vascular tissue. The vascular sleeve may be made of polytetrafluoroethylene (PTFE) material or the like. And the vascular clamp may come in different sizes suitable for different specific applications such as repair to small or large vascular structures and/or repairing gastrointestinal vessels.

BRIEF DESCRIPTION OF THE DRAWINGS

FIG. 1 A-B shows a damaged blood vessel before and after repair with a magnetic vascular clamp according to an embodiment of the present invention.

FIG. 2 A-B shows elevated perspective views of the structure of one embodiment.

FIG. 7 A-C shows an embodiment of a vascular clamp having multiple separate ratchet clamps.

DETAILED DESCRIPTION OF SPECIFIC EMBODIMENTS

Figure 3:
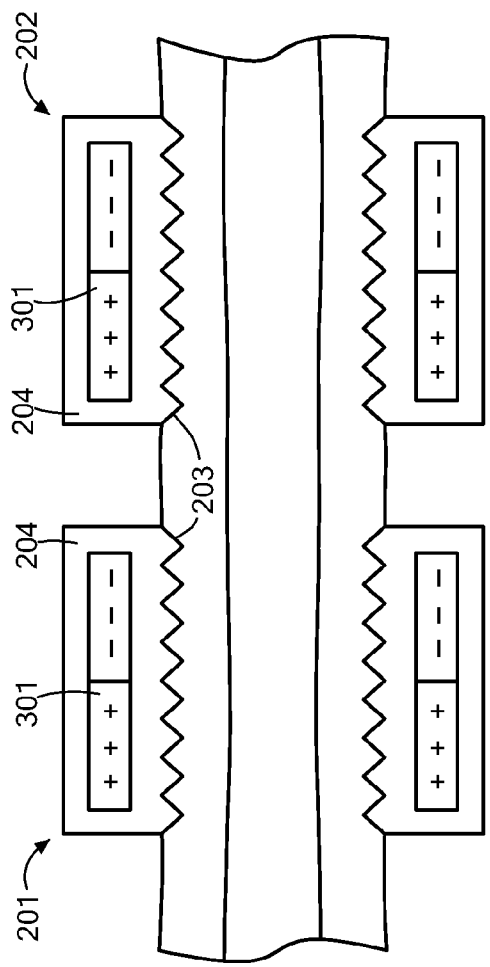
FIG. 3 shows the magnetic field arrangement according to one embodiment.

Embodiments of the present invention are directed to a various vascular clamp devices for vascular repair. As shown in FIG. 1A, a damaged blood vessel allows blood to leak out from within. A vascular clamp 100 fits over the damaged section of blood vessel as shown in FIG. 1B to occlude blood flow and support the structure of the enclosed vascular tissue.

FIG. 2 A-B shows elevated perspective views of the structure of a magnetic vascular clamp 200 according to one embodiment. There are two clamp pieces 201 and 202 each of which forms a partial cylindrical section of an annular cylinder. Each clamp piece 201 and 202 has an outer surface 205 and an inner surface 203 across which are arranged a plurality of structural ribs 206 from one sectional end to the other.

Figure 4:
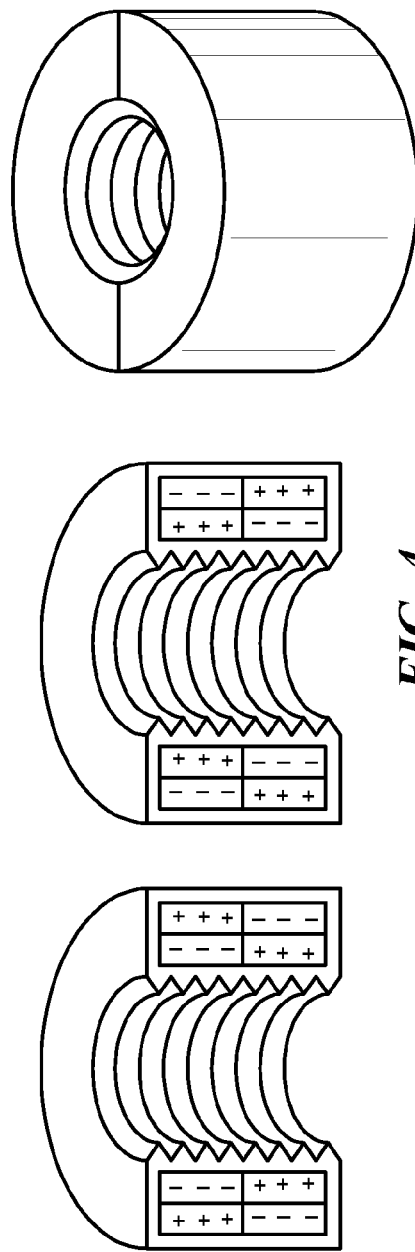
FIG. 4 shows the magnetic field arrangement in another embodiment.

Each clamp piece 201 and 202 also has a pair of magnetic sectional end surfaces 204 connecting the outer surface 205 and the inner surface 203 and having a characteristic magnetic field arrangement 301 as shown in FIG. 3. In the specific embodiment shown in FIG. 3, each magnetic field arrangement 301 actually is made up of multiple different magnetic field directions. FIG. 4 shows the magnetic field arrangement in another embodiment having a more complicated system of multiple magnetic field arrangements. A magnetic rare earth magnet material such as samarium cobalt or neodymium may be used in each clamp piece 201 and 202 for developing the magnetic field arrangements 301.

The sectional end surfaces 204 and the corresponding magnetic field arrangement 301 of each clamp piece 201 and 202 cooperate with the sectional end surfaces 204 and magnetic field arrangement 301 of the other clamp piece 202 and 201 to form a complete annular cylinder held together by the magnetic interaction between the magnetic field arrangements 301. As a result, the clamp pieces 201 and 202 together form a complete magnetic vascular clamp 200 that encloses an inner cylinder which structurally supports damaged vascular tissue therein with minimal fluid leakage.

Some embodiments may further have an outer encapsulation layer of bioinert material such as gold or titanium which covers some or all of each clamp piece 201 and 202. For example, some or all of the outer surface 205 and/or the inner surface 203 of each clamp piece 201 and 202 may have such a bioinert encapsulation layer. In addition or alternatively, there also may be a therapeutic coating on the inner surface 203 of each clamp piece 201 and 202 to promote healing of the enclosed vascular tissue.

Figure 5A:
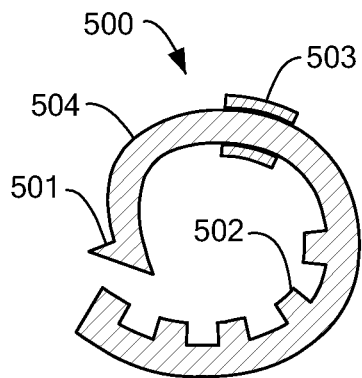
FIG. 5 shows an embodiment of a vascular clamp having a ratchet clamp with inward facing ratchet teeth.
Figure 5B:
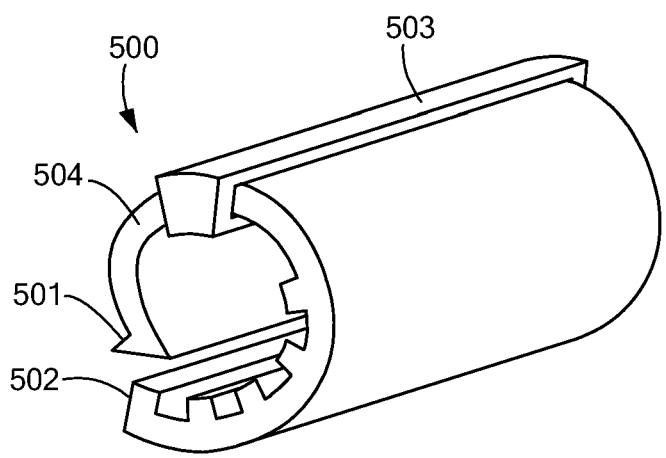
Figure 6:
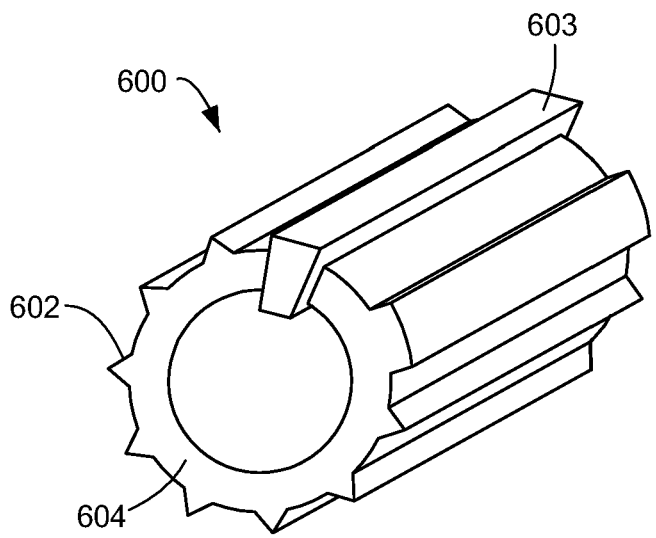
FIG. 6 shows an embodiment of a vascular clamp having a ratchet clamp with outward facing ratchet teeth.

Embodiments of the present invention also include a vascular clamp for vascular repair such as the ones shown in FIGS. 5-7 based on having a flexible planar clamp surface that cylindrically encloses a section of vascular tissue with minimal fluid leakage and at least one ratchet clamp having an end pawl and a plurality of ratchet teeth that cooperate in locking engagement to maintain the clamp surface around the enclosed vascular tissue.

FIG. 5 shows a cross-section and elevated side perspective of one such specific embodiment of a vascular clamp 500 having a flexible planar clamp surface 504 made of an appropriate bioinert material, for example, titanium or polytetrafluoroethylene (PTFE). Integrated into a single common structure with the clamp surface 504 is a ratchet clamp locking mechanism that includes an end pawl 501 along one end of the clamp surface 504, and a plurality of ratchet teeth 502 on the inner face of the clamp surface 504. The end pawl 501 and the ratchet teeth 502 cooperate together in locking engagement to maintain the clamp surface 504 around the enclosed vascular tissue with minimal fluid leakage. Locking bar 503 locking bar is slidably engageable to fit over the end pawl 501 to lock it into the locking engagement with the ratchet teeth 502.

FIG. 6 shows another embodiment of a vascular clamp 600 having ratchet teeth 602 that face radially outward away from the enclosed vascular tissue. FIG. 6 also shows the locking bar 603 slid over the end pawl to lock it into place. FIG. 7 A-C shows another embodiment based on a plurality of individual ratchet clamps 701 that fit over the clamp surface 702. Such an arrangement allows each specific structure to be made of a different material optimally suited for its specific function. For example, titanium or the like may usefully provide the required strength for the ratchet clamps 701, while a porous mesh of polytetrafluoroethylene (PTFE) material (e.g., Gore Tex™) may provide desirable sealing characteristics for the clamp surface 702.

Figure 8A:
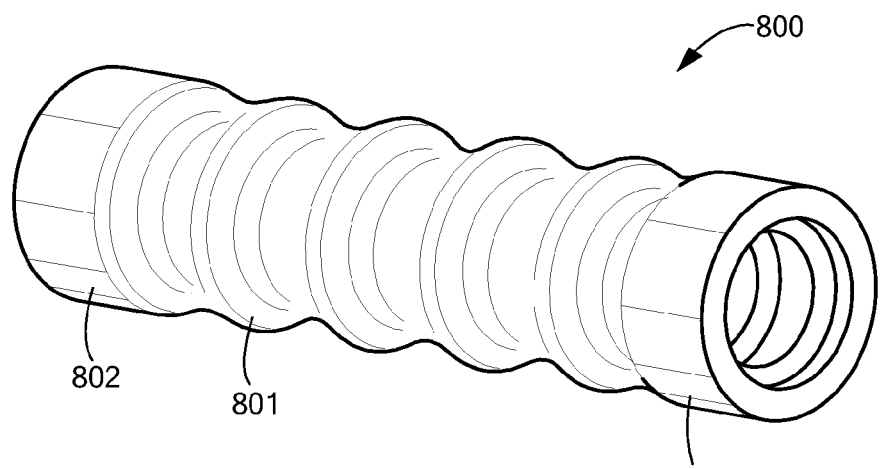
FIG. 8 A-B shows an embodiment of a vascular clamp having a cylindrical bellows sleeve.
Figure 8B:
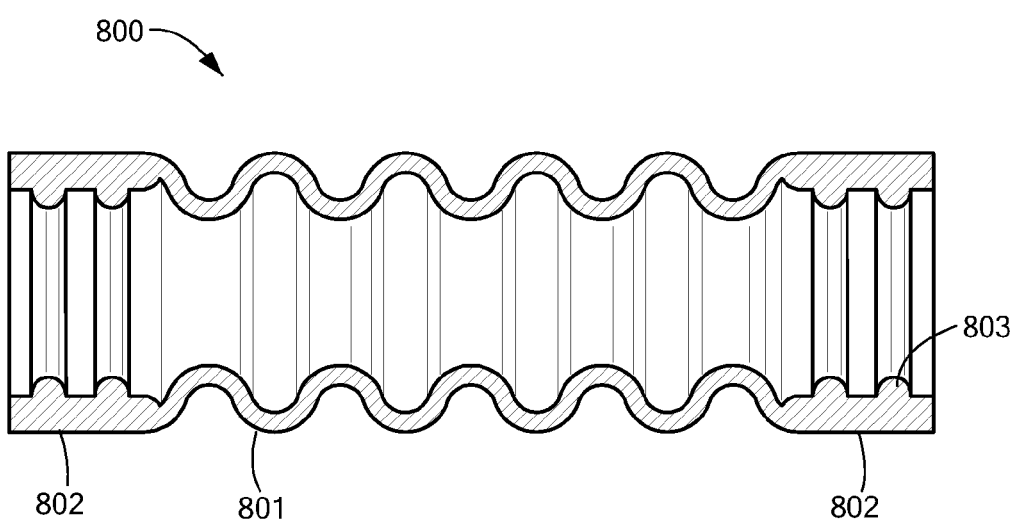
Figure 9C:
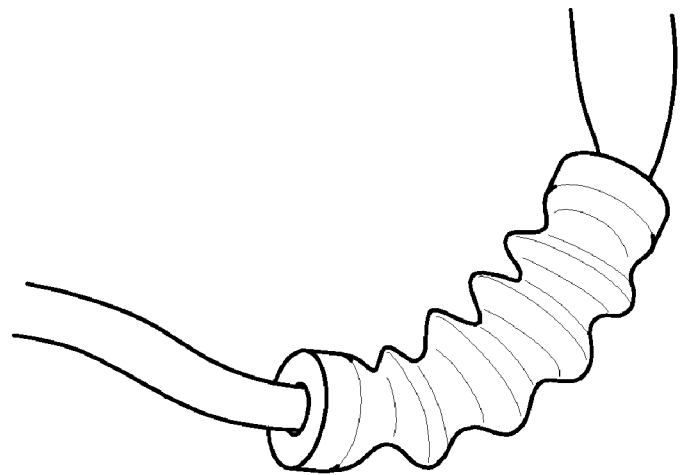
FIG. 9 A-C shows examples of vascular clamps as in FIG. 8 for different sized applications within a patient body.
Figure 9B:
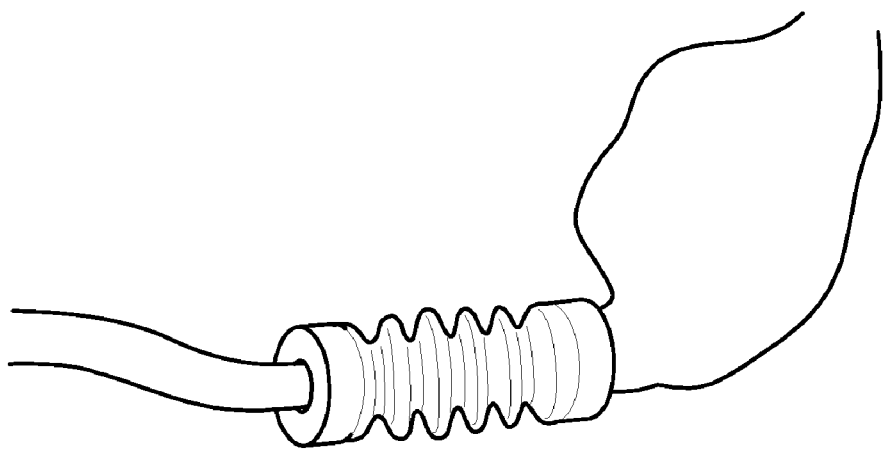
Figure 9A:
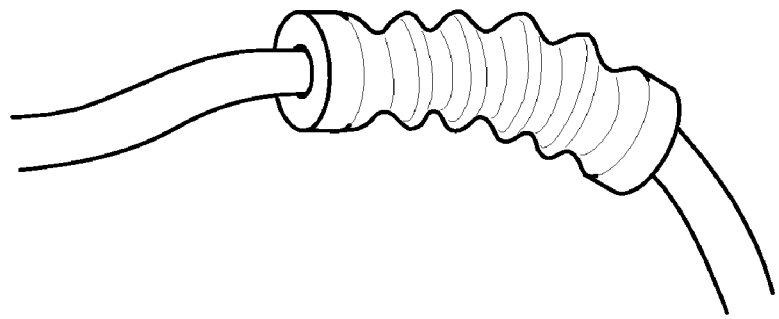

Embodiments of the present invention also include a vascular clamp 800 for vascular repair as shown in FIG. 8, which has a vascular sleeve 801 made of polytetrafluoroethylene (PTFE) material that forms a flexible cylindrical bellows that cylindrically encloses a section of vascular tissue to allow freely movement of the enclosed vascular tissue within the vascular sleeve 801. At each cylindrical end of the vascular sleeve 801, there is a sleeve anchor ring 802 that forms a fixed seal with underlying vascular tissue to minimize fluid leakage from within the vascular clamp 800. In the specific embodiment shown in FIG. 8, each sleeve anchor ring 801 includes a plurality of sealing ribs 803 for sealing with the underlying vascular tissue. Such vascular clamps 800 may come in different sizes as shown in FIG. 9 which are suitable for different specific applications such as repair to small vascular structures (FIG. 9A), larger vascular structures such as cardiac arteries (FIG. 9B), and/or repairing gastrointestinal tract and ducts (FIG. 9C).

Although various exemplary embodiments of the invention have been disclosed, it should be apparent to those skilled in the art that various changes and modifications can be made which will achieve some of the advantages of the invention without departing from the true scope of the invention.

What is claimed is:

1. A magnetic vascular clamp for vascular repair comprising:

first and second clamp pieces, each clamp piece forming a partial cylindrical section of an annular cylinder, and each clamp piece including:
i. an outer surface and an inner surface,
ii. a plurality of structural ribs arranged across the inner surface from one sectional end to the other, and
iii. a pair of magnetic sectional end surfaces connecting the outer surface and the inner surface and having a characteristic magnetic field arrangement;

wherein the sectional end surfaces and magnetic field arrangements of each clamp piece cooperate with the sectional end surfaces and magnetic field arrangements of the other clamp piece to form a complete annular cylinder held together by the magnetic field arrangements and enclosing an inner cylinder so as to structurally support damaged vascular tissue therein with minimal fluid leakage.

2. A magnetic vascular clamp according to claim 1, wherein each magnetic field arrangement includes a plurality of magnetic field directions.

3. A magnetic vascular clamp according to claim 1, wherein each clamp piece includes a magnetic rare earth magnet material for developing the magnetic field arrangements.

4. A magnetic vascular clamp according to claim 3, wherein the magnet material includes one or more of samarium cobalt and neodymium material.

5. A magnetic vascular clamp according to claim 1, further comprising:
an outer encapsulation layer covering at least a portion of each clamp piece.

6. A magnetic vascular clamp according to claim 5, wherein the encapsulation layer covers the entire clamp piece.

7. A magnetic vascular clamp according to claim 5 wherein the encapsulation layer includes gold or titanium.

8. A magnetic vascular clamp according to claim 1, further comprising:
a therapeutic coating on the inner surface of each clamp piece to promote healing of the enclosed vascular tissue.

* * * * *